(12) United States Patent
Shen et al.

(10) Patent No.: US 9,145,472 B2
(45) Date of Patent: Sep. 29, 2015

(54) CHARGE REVERSIBLE POLYMERS

(75) Inventors: Youqing Shen, Laramie, WY (US);
Peisheng Xu, West Lafayette, IN (US)

(73) Assignee: Wyoming Research Products Center, Laramie, WY (US)

( * ) Notice: Subject to any disclaimer, the term of this patent is extended or adjusted under 35 U.S.C. 154(b) by 0 days.

(21) Appl. No.: 13/033,247

(22) Filed: Feb. 23, 2011

(65) Prior Publication Data
US 2011/0244046 A1    Oct. 6, 2011

Related U.S. Application Data

(60) Division of application No. 12/242,191, filed on Sep. 30, 2008, now abandoned, which is a continuation of application No. PCT/US2007/015447, filed on Jul. 5, 2007.

(60) Provisional application No. 60/818,882, filed on Jul. 6, 2006, provisional application No. PCT/US2007/008146, filed on Apr. 2, 2007, provisional application No. 60/787,789, filed on Mar. 31, 2006.

(51) Int. Cl.
| | |
|---|---|
| *C08G 73/00* | (2006.01) |
| *C08G 73/02* | (2006.01) |
| *C08G 69/02* | (2006.01) |
| *A61K 8/02* | (2006.01) |
| *A61K 47/30* | (2006.01) |
| *A61K 9/00* | (2006.01) |
| *A61K 9/107* | (2006.01) |
| *A61K 31/785* | (2006.01) |
| *A61K 47/48* | (2006.01) |

(52) U.S. Cl.
CPC ........... *C08G 73/0206* (2013.01); *A61K 8/0291* (2013.01); *A61K 9/0019* (2013.01); *A61K 9/1075* (2013.01); *A61K 31/785* (2013.01); *A61K 47/30* (2013.01); *A61K 47/482* (2013.01); *A61K 47/488* (2013.01); *A61K 47/48107* (2013.01); *A61K 47/48192* (2013.01); *A61K 47/48315* (2013.01); *C08G 69/02* (2013.01); *C08G 73/00* (2013.01)

(58) Field of Classification Search
CPC .... C08G 73/0206; C08G 73/00; C08G 69/02; A61K 8/0291
USPC ............................ 424/400, 486, 1.29; 516/98
See application file for complete search history.

(56) References Cited

U.S. PATENT DOCUMENTS

| | | | | |
|---|---|---|---|---|
| 6,048,736 | A * | 4/2000 | Kosak ........................... | 436/536 |
| 6,613,879 | B1 * | 9/2003 | Firestone et al. ............. | 530/330 |

* cited by examiner

*Primary Examiner* — David Lukton
(74) *Attorney, Agent, or Firm* — Davis, Brown, Koehn, Shors & Roberts, P.C.; Kent A. Herink

(57) ABSTRACT

Described are charge reversible polymers, peptides and their resulting colloidal particles, comprising polymers and peptides having primary and secondary amines that are protected as easily hydrolysable amides. The amides are charge-reversible such that at neutral pH they are negatively charged but become positively charged at pH less than 6 and thus are relatively stable at neutral pH but quickly hydrolyze at pH below 6. Incorporating a drug in a micelle or a polymer comprised of the charge-reversible polymers or peptides provides a drug carrier for delivering the drug preferentially to the solid tumor or other targeted cells.

6 Claims, 12 Drawing Sheets

CHARGE REVERSIBLE POLYMERS

This application is a divisional of application Ser. No. 12/242,191, filed Sep. 30, 2008, now abandoned, which is a continuation of PCT/US07/15447, filed Jul. 5, 2007, which claims priority to provisional application 60/818,882, filed Jul. 6, 2006; Application Ser. No. 12/242,191 also claims priority to PCT/US07/08146, filed Apr. 2, 2007, which claims priority to provisional application 60/787,789, filed Mar. 31, 2006.

The United States Government has rights in this invention under the National Science Foundation (BES-0401982) and the American Cancer Society (RSG-06-11821-CDD).

BACKGROUND OF THE INVENTION

The invention relates generally to charge reversible polymers, peptides and their resulting colloidal particles and, more specifically, to easily hydrolysable amides that are relatively stable at neutral pH but quickly hydrolyze at low pH.

Cationization is a potent approach to enhance cellular uptake by electrostatically adsorptive endocytosis of macromolecules and colloidal particles such as proteins, nanoparticles and liposomes. For instance, cationic photosensitizer chlorine-6 (ce6)-conjugate with cationic polylysine had up to 17 times higher cellular uptake of ce6. This enhanced endocytosis is of great importance in cancer-targeted drug delivery because intracellular drug release from liposomes, polymer-drug conjugates, and polymeric micelles or nanoparticles can circumvent membrane-associated multidrug resistance. Cationic polymers such as polyethyleneimine (PEI) can also disrupt lysosomal membranes, which is useful for drug delivery to cytosol. Nuclear localization signals (NLS), which are short highly positively charged basic peptides that actively transport large molecules across the nuclear membrane and localize cargo molecules (to which they have been conjugated) from the cytosol to the cell nucleus, is also useful for nuclear drug/gene delivery.

The in vivo applications of those positively charged macromolecules or colloidal particles, however, is very limited because cationic charges can cause severe serum inhibition and rapid clearance from the plasma compartment, and sequestered to mainly in the liver. For instance, a cationized antibody had a 58-fold increase in the systemic clearance from the plasma compartment and a 9-fold reduction in the mean residence time as compared to the native antibody. Such a fast plasma clearance makes them impossible to reach their targeted tissues other than the liver or intracellular compartment.

Most cancer chemotherapy drugs, such as anthracyclines and cisplatin, target nuclear DNA to cause DNA damage and/or topoisomerase inhibition to induce cell death (apoptosis). In addition to the overexpressed multidrug-resistance mechanism in the cell membrane, drug-resistant cancer cells have many intracellular drug-resistance mechanisms to limit the access of cytosolic drugs to the nucleus. Consequently, only a small percentage of drugs delivered into the cytosol finally reach the nucleus. For example, less than 1% of the cisplatin molecules that enter the cell actually bind the nuclear DNA. Thus, a drug carrier capable of localizing and directly releasing drugs into the nucleus would circumvent the multidrug-resistance and intracellular drug-resistance mechanisms to effectively deliver drugs to the vicinity of DNA, leading to a high therapeutic efficacy.

Polymer nanoparticles can carry drugs preferentially to cancerous tissues by means of the enhanced permeation and retention (EPR) effect and bypass the multidrug resistance in the cell membrane, but the nanoparticles developed to date were found retained in cytoplasmic organelles including lysosomes rather than the nucleus. Nuclear localization peptides (NLPs)—short highly positively charged peptides that actively transport large proteins across the nuclear membrane—have been used to localize drug molecules from the cytosol to the nucleusA cationic polymer, polyethyleneimine (PEI), has been used extensively in nonviral gene delivery. It can carry DNA across the cell membrane, harness the molecular motors to actively move along the microtubule network, and finally enter the nucleus. NLPs and PEI, however, are highly positively charged at physiological pH. Positively charged polymers or colloidal particles can cause severe serum inhibition and are rapidly cleared from the plasma compartment, and thus cannot be used in vivo.

An ideal regime would be to activate the cationic charges only in cancerous tissues or their intracellular compartments. In the present invention, nanoparticles with a negative-to-positive charge-reversal PEI outer layer triggered by the solid tumor extracellular acidity (pH<7) or lysosomal (pH 4-5) for nuclear drug delivery. Negatively charged polymers have little interaction with the blood components and have been used extensively in vivo.

SUMMARY OF THE INVENTION

The present invention relates to charge reversible polymers, peptides and their resulting colloidal particles. Their primary and secondary amines are protected as easily hydrolysable amides. The amides are relatively stable at neutral pH but quickly hydrolyze at low pH. These polymers, peptides or particles are thus charge-reversible: at neutral pH they are negatively charged but become positively charged at acidic pH. One of the applications of these charge-reversible polymers, peptides or particles is as carriers for drug delivery to solid tumors and lysosomes, where the pH can be as low as 6, and 4-5, respectively. The present invention discloses a technique that can preserve the amine groups as negatively charged groups that have no or low interactions with cells and low toxicity. These groups are stable at neutral pH but rapidly decompose and convert back to amine groups at pH less than 7. This technique has many applications including their development as drug or gene delivery carriers.

In a preferred embodiment of the invention, nanoparticles with a negative-to-positive charge reversal outer layer, such as PEI, that is triggered by the solid tumor extracellular or lysosomal acidity for nuclear drug delivery.

DESCRIPTION OF THE INVENTION

Experimental Procedures

Materials N-hydroxysuccinimide (NHS) (98%) was purchased from Alfa Aesar. Polyethylenimine (PEI, branched, Mw 1.8 KDa, 25% $NH_2$, 50% NH and 25% N) was purchased from Polysciences. ε-Caprolactone (ε-CL) (Aldrich) was dried over calcium hydride. Dimethyl sulfoxide (DMSO) and octanoic acid (Aldrich) were dried over 4 Å molecular sieve. All other chemicals otherwise stated were from Aldrich and used without further purification.

Example 1

Figure 3A:
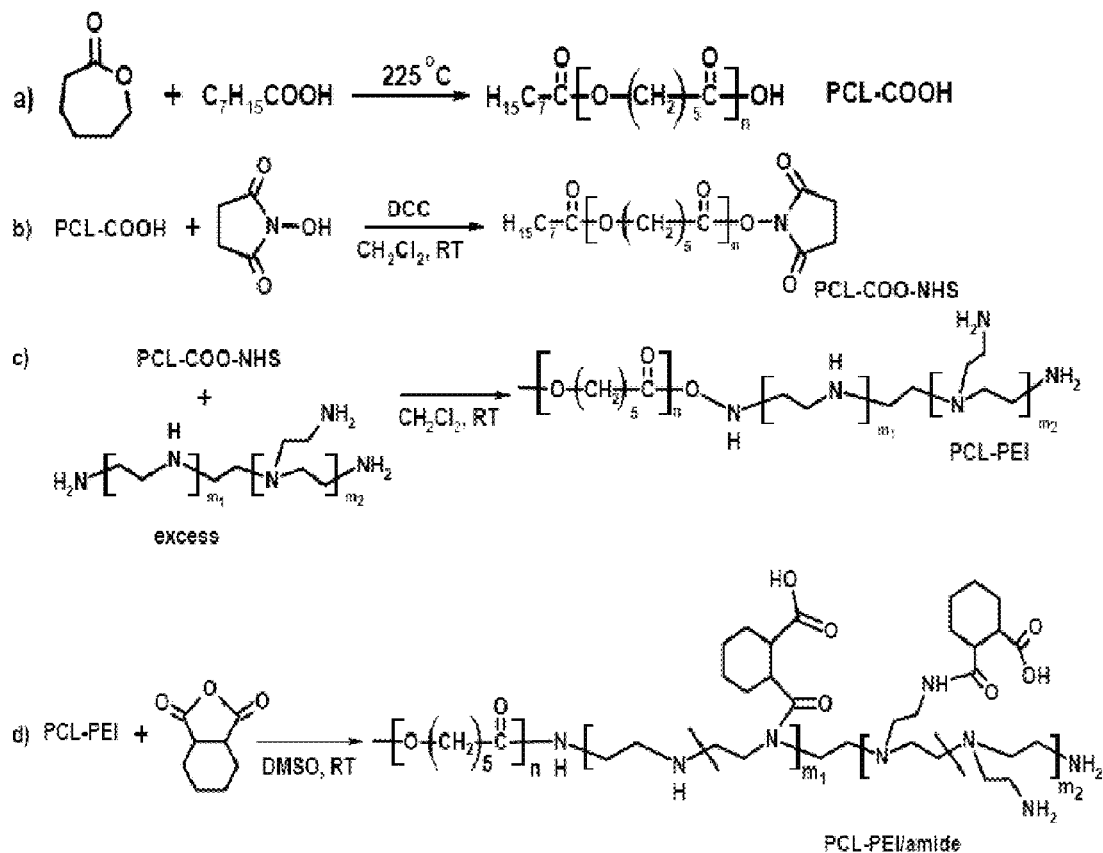
FIGS. 3A and 3B are schematic diagrams of the synthesis of folic acid functionalized poly(ε-caproactone)-block-polyethyleneimine (PCL-PEI-FA) and the subsequent amide product (PCL-PEI/amide-FA).
Figure 3B:
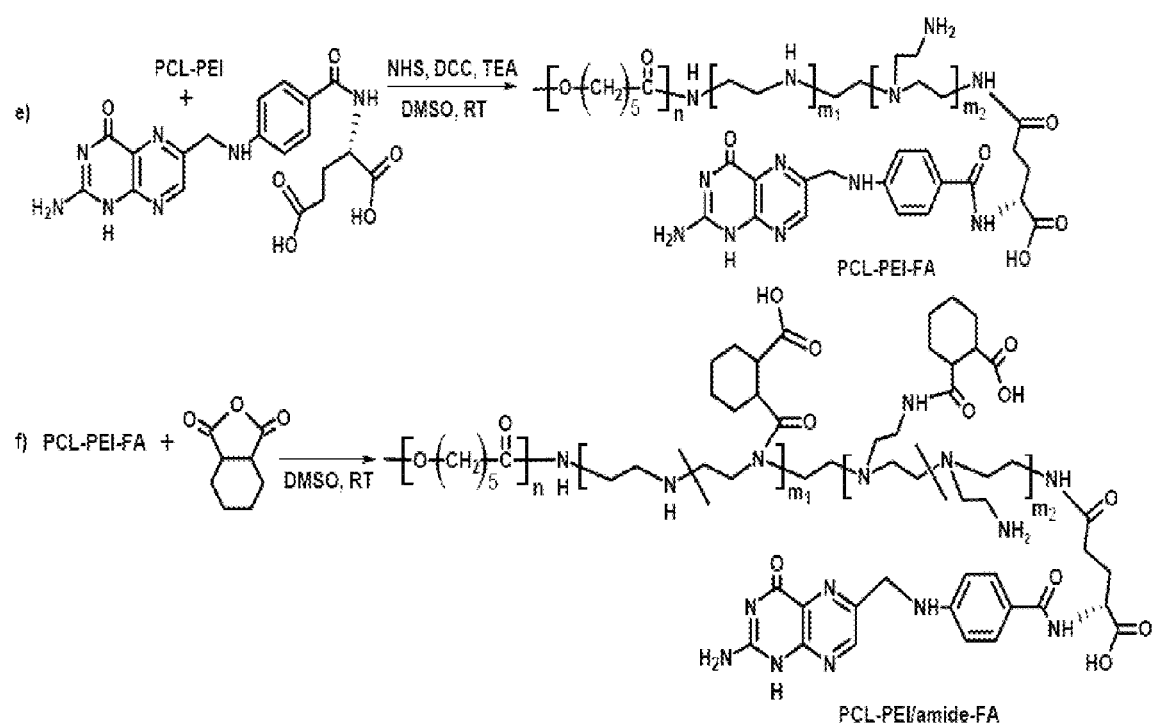

Polymer Synthesis (Scheme 3—FIG. 3)

Synthesis of poly(ε-caprolactone) (PCL) (a): ε-Caprolactone (ε-CL) (12.5 mL, 113 mmol) and octanoic acid (1.75 mL, 11 mmol) were charged into a flask. The flask was sealed with a rubber septum and degassed. It was heated at 225° C. for 3.5 h with magnetic stirring. The solid was cooled to about 60° C. and dissolved in THF. The solution was poured into 10-fold cold methanol to remove the unreacted monomer. The solid was isolated and purified by reprecipitation. It then was dried under high vacuum at 60° C. PCL with a terminal carboxylic acid (PCL-COOH) (11.8 g, yield 47%) was obtained. 1H-NMR (400 MHz, $CDCl_3$): δ (ppm): 4.08 (t), 2.32 (t), 1.71-1.57 (m), 1.42-1.34 (m), 0.88 (t). Its molecular weight was 3.8 KDa determined by NMR, and 3.2 KDa determined by gel permeation chromatography with polydispersity index of 1.15.

Synthesis of PCL-COO—NHS (b): PCL-COOH (2.45 g, 0.64 mmol), N-hydroxysuccinimide (NHS, 0.38 g, 3.3 mmol) and 1,3-dicyclohexylcarbodiimide (DCC, 0.67 g, 3.3 mmol) were charged into a 50 mL flask and dissolved in 20 mL of dichloromethane. The reaction solution was stirred at room temperature for 48 h, and then filtered. The filtrate was poured into a large excess of dry ether. The solid was isolated and reprecipitated twice. The product was dried under high vacuum at room temperature for 8 h. PCL with a terminal NHS ester (PCL-COO—NHS) was obtained (1.74 g, 71%). 1H-NMR (400 MHz, $CDCl_3$): δ (ppm): 4.08 (t), 2.85 (m), 2.32 (t), 1.71-1.57 (m), 1.45-1.32 (m), 0.88 (t).

Synthesis of PCL-PEI (c): PCL-COO—NHS (1.74 g, 0.45 mmol) and PEI (Mn of 1.8 KDa, 8.3 g, 4.6 mmol) were separately dissolved in 20 mL of dichloromethane. The PCL-COO—NHS solution was dropwise added into the PEI solution with stirring. The reaction was continued with the protection of nitrogen at room temperature for 48 h. The solution was then washed twice with 100 mL of water. The organic phase was precipitated in diethyl ether and dried under high vacuum at 40° C. for 8 h. PCL-block-PEI (PCL-PEI) was obtained (0.92 g, 53% yield). $^1$H NMR (400 MHz, $CDCl_3$): δ (ppm): 4.08 (t), 2.81-2.60 (m), 2.32 (t), 1.69-1.61 (m), 1.43-1.30 (m), 0.88 (t). The chain ratio PCL/PEI calculated from the NMR spectrum was 1.07. GPC showed that there was no unreacted PCL in the block copolymer.

Synthesis of PCL-PEI/amide (d): PCL-PEI (0.1 g, 0.018 mmol, equivalent to 0.567 mmol of NH2 and NH) was dissolved in 5 mL of DMSO in a 25 mL flask with a magnetic stirring bar. 1,2-cis-Cyclohexanedicarboxylic anhydride (16 mg, 0.10 mmol) was added. The reaction was kept at room temperature with the protection of nitrogen for 48 h. The mixture was precipitated in diethyl ether. The solid was isolated and purified by reprecipitation twice. It was dried under high vacuum at 40° C. for 8 h. PCL-PEI/amide was obtained (0.06 g, 60% yield). 1H NMR (400 MHz, d6-DMSO): δ (ppm): 4.00 (t), 2.81-2.50 (m, overlapped with the solvent), 2.26 (t), 1.64-1.49 (m), 1.47-1.21 (m), 0.88 (t). The calculation from the $^1$H-NMR spectrum showed that 23% of the amine groups (NH2+NH) of the PEI block were converted to their amides.

Synthesis of PCL-PEI-FA (e): PCL-PEI (0.5 g, equivalent to 2.84 mmol of NH2 and NH), DCC (344.6 mg, 1.7 mmol), NHS (204 mg, 1.7 mmol), folic acid (39.3 mg, 0.09 mmol) were charged into a 25 mL flask and dissolved in 10 mL of DMSO. Triethylamine (TEA, 1.7 mL) was added to the solution. The reaction was kept at room temperature with the protection of nitrogen for 48 h. The mixture was purified by repeated precipitated in diethyl ether. The raw product was further purified by dialysis in DI water (Spectra Por-7, MWCO 3,500) to remove the unreacted folic acid. The resulting product was dried under high vacuum at 40° C. for 8 h to give final product 0.35 g (yield 70%). 1H-NMR (400 MHz, d6-DMSO): δ (ppm): 8.52 (s), 8.00 (s), 7.56 (s), 6.62 (s), 4.42 (s), 3.98 (t), 2.81-2.50 (br, overlapped with the solvent), 2.26 (t), 1.64-1.49 (m), 1.47-1.21 (br), 0.88 (t). The 1H-NMR spectrum showed that on average each PCL-PEI chain had 0.79 folic acid molecule.

Synthesis of PCL-PEI/amide-FA (f): PCL-PEI-FA (0.35 g, equivalent to 1.89 mmol of NH2 and NH) was dissolved in 10 mL of DMSO in a 25 mL flask with a magnetic stirring bar. 1,2-cis-Cyclohexanedicarboxylic anhydride (52.5 mg, 0.34 mmol) was added. The reaction was kept at room temperature with the protection of nitrogen for 48 h. The mixture was precipitated in diethyl ether. The solid was isolated and purified by repeated precipitation. It was dried under high vacuum at 40° C. for 8 h. PCL-PEI/amide-FA was obtained (0.25 g, 71% yield). 1H NMR (400 MHz, DMSO): δ (ppm): 8.65 (s), 8.14 (s), 7.65 (s), 6.64 (d), 4.49 (s), 4.02 (t), 2.80-2.45 (br, overlapped with the solvent), 2.27 (t), 1.74 (s), 1.64-1.49 (m), 1.47-1.21 (br), 0.88 (t). The 1H-NMR spectrum showed that about 17.6% of the PEI amine groups were amidized.

Example 2

Figure 4:
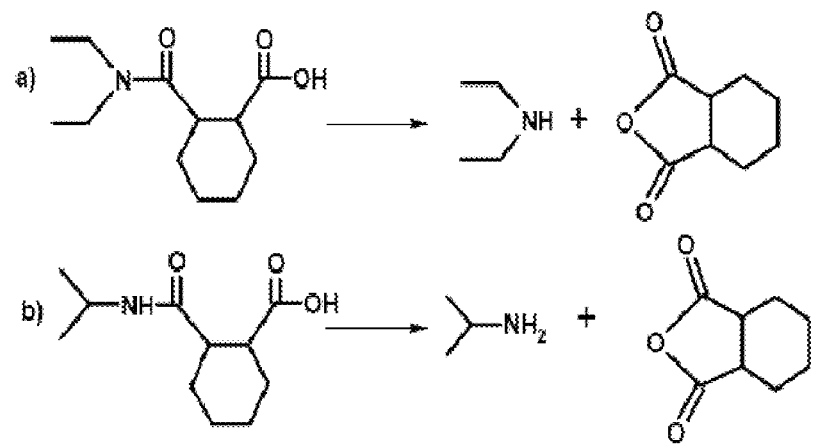
FIG. 4 is a schematic diagram of the hydrolysis of model compounds 2-[(diethylamino)carbonyl]cyclohexanecarboxylic acid and 2-[(isopropylamino)carbonyl]cyclohexanecarboxylic acid.

Model compound synthesis and hydrolytic kinetics measurement (Scheme 4—FIG. 4): Briefly, N,N-diethylamine (415 μL, 4 mmol) and 1,2-cis-cyclohexanedicarboxylic anhydride (617 mg, 4 mmol) were dissolved in 10 mL dichloride methane. The reaction was kept at room temperature for 2 h with stirring. The solvent was then removed by rotary evaporation to obtain the raw product. The raw product was purified by recrystallizing from benzene to get 2-[(diethylamino)carbonyl]cyclohexanecarboxylic acid. 1H NMR (400 MHz, CDCl$_3$): δ (ppm): 3.60-3.22 (m), 2.77 (m), 2.51-2.45 (m), 1.87-1.66 (m), 1.58-1.46 (m), 1.49-1.39 (m), 1.28 (q), 1.17 (t). Similarly, 2-[(isopropylamino)carbonyl]cyclohexanecarboxylic acid was synthesized. 1H NMR (400 MHz, CDCl$_3$): δ (ppm): 3.83 (q), 2.73 (q), 2.64 (q), 1.87 (m), 1.79 (m), 1.64 (m), 1.45 (m), 1.33 (m), 1.01 (d).

The hydrolysis of the model compounds was monitored by 1H-NMR. Briefly, 2-[(isopropylamino)carbonyl]cyclohexanecarboxylic acid (10 mg) was dissolved in 2 mL D2O. Sodium carbonate was used to adjust the solution pH to 5.0, 6.0 or 7.4 at 37° C. At predesigned time intervals, 1HNMR spectra of the solution were measured on a Bruker Avance DRX-400 spectrometer. The hydrolysis was monitored by measuring the integrations of the peaks at 3.77-3.9 ppm (CH in the amide of propan-2-amine) and the 3.3-3.5 ppm (CH in the propan-2-amine).

Example 3

The amide hydrolysis kinetics of TCRNs: The hydrolysis of the amides in the TCRNs was monitored by 1H-NMR. The TCRNs in DI water were prepared as described above. The nanoparticle solution was adjusted to pH of 5.0, 6.0 or 7.4, respectively, at a concentration of 1 mg/mL. DMF (1 μl) was added to the solution as the internal standard. These solutions were immersed in a 37° C. water bath. At predesigned time intervals, the TCRN solution (0.5 ml) was sampled and filtered using Centricon centrifugal filter devices (YM-3, 3,000 MWCO, Millipore Corp., Bedford, Mass.). The percentage of hydrolyzed amides was calculated from the integrations of the reference peak at 3.0-2.7 ppm (DMF signal) and the peak at 1.7-1.0 ppm of free 1,2-cis-cyclohexanedicarboxylic acid hydrolyzed from the amides.

Example 4

TCRN size and zeta potential measurements: The sizes (diameter) of CRNs, TCRNs, and TCRNs/DOX nanoparticles were determined using a Nano-ZS zetasizer (Malvern Instrument Ltd., UK) with a laser light wavelength of 632.8 nm and a scattering angle at 173°. The nanoparticles were prepared as described above. The zetasizer was routinely calibrated with a 60 nm Nanosphere™ standard (Duke Scientific Corp. CA). Each measurement was performed in triplicate, and the results were processed with DTS software version 3.32.

The zeta-potentials of the nanoparticles were determined by phase analysis light scattering technology using the zetasizer (Malvern Instrument), which was routinely calibrated with a −50 mV zeta potential standard (Malvern Instruments). The nanoparticles were dispersed in 20 mL of buffer at pH 5.0, 6.0, or 7.4 at 0.1 mg/mL with stirring. The measurements were performed in disposable zeta capillary cells at 37° C. The attenuator was set at 9 and the F (Ka) value was set at 1.5. Each measurement was performed for 30 runs, and the results were processed with DTS software version 3.32.

Example 5

Hemolytic activity of nanoparticles on red blood cell (RBCs): Mouse blood was collected in heparin-containing eppendorf, and then centrifuged at 1,000×g for 5 min to separate the RBCs from the plasma. The RBCs were dispersed in Alsever's Buffer. The RBC suspension (600 μL) was washed 5-6 times by centrifugation (1,000×g, 3 min) until the cell suspension became clear, and then diluted in 4000 μl GVB buffer to obtain RBC stock solution. The nanoparticle solution (100 μL at 0, 2, 4, 8, 40, or 80 μg/mL in PBS), GVB buffer (200 μL), and the RBC stock solution (100 μL) were added to tubes respectively. The tubes were incubated at 37° C. for 1 h. Then, 2 mL of 0.15 M NaCl was added to each tube. The tubes were centrifuged (1,000×g, 3 min) to separate the intact RBCs. The supernatant solutions were collected. Absorbance of hemoglobin in the supernatant was measured at 412 nm using a UVVIS spectrophotometer. Standard 100%, 50%, 0% hemolysis solutions were made from following solutions: 50 μL cell solution/450 μL H2O/500 μL 0.3M NaCl/50 μL PBS/100 μL GVB buffer, 25 μL cell solution/475 μL H2O/500 μL 0.3M NaCl/50 μL PBS/100 μL GVB buffer, and 500 μL H2O/500 μL 0.3 M NaCl/50 μL PBS/100 μL GVB buffer, respectively. The cell hemolysis percentage was calculated by Hemolysis (%)=(Abs−Abs0)/(Abs100−Abs0)×100, Where Abs, Abs100, and Abs0 are the absorbances of the sample, the 100% hemolysis solution, and the 0% hemolysis solution respectively. All hemolytic experiments were carried out in triplicates.

Example 6

Cellular Localization of TCRNs by Confocal Scanning Laser Microscopy a) TCRNs/DOX: SKOV-3 ovarian cancer cells were obtained from American Type Culture Collection (ATCC, Rockville, Md.). The cells were plated into glass-bottom petri dishes (MatTek, Ashland, Mass., no. P35G-1.0-14-C) at 80,000 cells per plate in 2 mL of RPMI-1640 medium (Sigma-Aldrich) supplemented with 10% fetal bovine serum, 10 μg/ml insulin, and antibiotic/antimycotic solution. They were incubated for 24 h at 37° C. and 5% CO2 before the treatments. Treatments were prepared in the RPMI medium containing 10 mM HEPES (pH 7.4). The TCRNs/DOX solution was added to the medium at the DOXequivalent dose of 1 μg/mL. Control experiments were carried out at the same time. After 1 h, lysotracker (Molecular Probes, Carlsbad, Calif.) was added to the wells at a concentration of 150 nM. The images were taken 1 h later using a confocal scanning laser microscope (Leica TCS SP2 microscope). Lysotracker was observed by using a 488-nm laser, and the emission wavelength was read from 510 to 540 nm and expressed as green. TCRNs/DOX were observed by using a 488-nm laser, and the emission wavelength was read from 560 to 610 nm and expressed as red. Images were produced by using the lasers sequentially with a 63× objective lens. Cells were kept at 37° C. and 5% CO2 except when being observed on the microscope.

b) TCRNs/PKH26 and the nuclear localization: TCRNs/PKH26 nanoparticles were prepared similarly to the preparation of TCRNs/DOX except that PKH26 were used. Treatments were prepared in RPMI medium containing 10 mM HEPES at pH 7.4. The TCRNs/PKH26 solution was diluted in the HEPES containing RPMI medium to make the same polymer concentration as the TCRNs/DOX treatment in a, and the cell culture with TCRNs/PKH26 was the same as that with TCRNs/DOX in a. After 12 or 24 h, DRAQ5™ (AXXORA LLC, San Diego, Calif.) was added to the wells at a concentration of 5 μM. The images were taken using confocal microscope. The nuclear staining was observed by using a 633-nm laser, and the emission wavelength was read from 660 to 810 nm and expressed as blue. TCRNs/PKH26 were observed using a 543-nm laser, and the emission wavelength was read from 560 to 610 nm and expressed as red. Images were processed with NIH ImageJ.

Example 7

Cellular uptake measured by flow cytometry: SKOV-3 cells were seeded in 6-well plates at a density of 1×106 cells per well in 2.5 mL RPMI-1640 medium and incubated in a humidified 5% CO2 atmosphere for 48 h. The original medium was replaced by fresh medium that were supplemented with free DOX, blank TCRNs, TCRNs/DOX, or TCRNs/DOX pretreated at pH 6 for 2 h, or DOX-loaded control nanoparticles CRNs (CRNs/DOX) at the same dose. The cells were incubated for 1 h at 37° C., and then washed three times with cold PBS, and harvested by trypsin treatment. The harvested cells were suspended in 1 mL of PBS containing 3% FBS (0.5 mL). The cell suspensions were centrifuged at 1000 rpm for 4 min at 4° C. The supernatants were discarded and the cell pellets were washed with 1 mL of PBS to remove the background fluorescence in the medium. After two cycles of washing and centrifugation, cells were resuspended and diluted to a final volume of 1 mL in PBS. Cells having DOX fluorescence were enumerated by fluorescence-activated cell sorting (FACS) (NPE Quanta™ system). Cells were excited with an argon laser (488 nm) and the signals were collected in the FL2 channel. Forward and side-scatter were "gated" to exclude dirt and clumped cells; gating was used identically on all analyses. Data were analyzed with WinMDI (version 2.8) software to obtain the DOX-positive cell percentage and relative fluorescent unit (RFU)/cell.

Example 8

In vitro cytotoxicity MTT assay: The cytotoxicity assay was carried out using the (3-(4,5-dimethylthiazolyl-2)-2,5-diphenyltetrazolium bromide) (MTT) cell proliferation kit (ATCC, Manassas, Va.) according to the modified manufacturer's protocol. SKOV-3 cells were seeded in 96-well plates at an initial density of 15,000 cells/well in 200 μL of RPMI medium. The cells were allowed to grow for 24 h. The original medium in each well was replaced with 100 μL of fresh medium. The free DOX or TCRNs/DOX solutions was added to the medium at concentrations ranging from 0.1 μg/mL to 10 μg/mL. Each dosage was replicated in 3 wells. Treated cells were incubated at 37° C. under a humidified air with 5% CO2 for 4 h. The medium in each well was then replaced with fresh culture medium and the cells were allowed to incubated for another 20 h. MTT reagent (10 μL) was added to each well and the cells were incubated for 2 h at 37° C. or until purple crystals were visible. Detergent reagent (100 μL) was added to each well and then the plates were placed in a 37° C. incubator for 2 h, or until all the crystals dissolved. The absorbance at 570 nm of the solution in each well was recorded using a microplate UVspectrometer (SpectraMax 384 Plus). Cell viability was calculated relative to the control.

Example 9

Amides with neighboring carboxylic acid groups exhibit pH-dependent hydrolysis. The hydrolysis of model amides of primary and secondary amines made from cis-1,2-cyclohexanedicarboxylic anhydride was tested at different pH values. The amide of the secondary amine almost instantly hydrolyzed at pH 5, slightly slower at pH 6, but only 50% even after 60 h at pH 7.4. The amide of the primary amine hydrolyzed more slowly at pH 5 and 6 than that of the secondary amine amide, and did not hydrolyze at pH 7.4. Thus, these types of amides were used to preserve the primary and secondary amines of PEI: At neutral pH, the amides are stable and negatively charged because of the β-carboxylic acid groups, while at a low pH, the amides hydrolyze to regenerate the amine groups to carry cationic charges.

Figure 5:
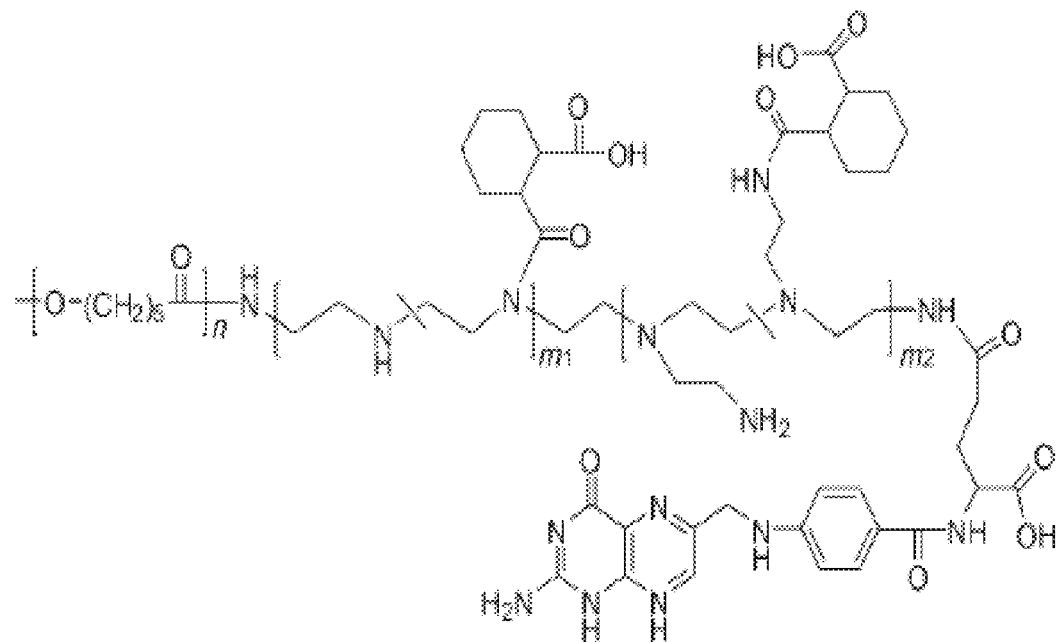
FIG. 5 is a schematic diagram of the structure of folic acid functionalized poly(e-caprolactone)-block-PEI with the amines converted into their amides (PCL-b-PEI/amide-FA).

To demonstrate this concept, a model polymer, polycaprolactone ($M_n$=3800)-block-PEI ($M_n$=1800) (PCLPEI) was synthesized (FIG. 3). Its PEI block reacted with 1,2-cyclohexanedicarboxylic anhydride to convert the primary and secondary amines into their amides (PCL-PEI/amide). The degree of amidization was optimized. The PEIblock with 20% of its primary and secondary amines converted into their amides was found optimal in terms of the charge-reversal kinetics of the resulting nanoparticles (Scheme 5—FIG. 5). Folic acid (FA) moieties were also conjugated to the PEIblock to form PCL-b-PEI/amide-FA for folate-receptor targeting. It was estimated from the NMR spectra that there were 0.79 molecules of folic acid per PCL-PEIchain on average. The PCL-PEI/amide-FA formed nanoparticles of about 210 nm in diameter in water. The nanoparticles were about 120 nm in diameter if loaded with 14.6 wt % doxorubicin (DOX). Transmission electron microscopy (TEM) showed that these nanoparticles were spherical.

The hydrolysis kinetics of the amides in the PCL-PEI/amide was determined by dispersing the nanoparticles in solution at pH 7.4, 6.0, or 5.0. The amides hydrolyzed to an extent of about 70% at pH 5.0 and 40% at pH 6.0 in 2 h. At pH 7.4, only about 25% of the amides hydrolyzed even after 24 h. The amides were hydrolyzed to more than 75% and 50% at pH values of 5.0 and 6.0, respectively, after 24 h.

Figure 6:
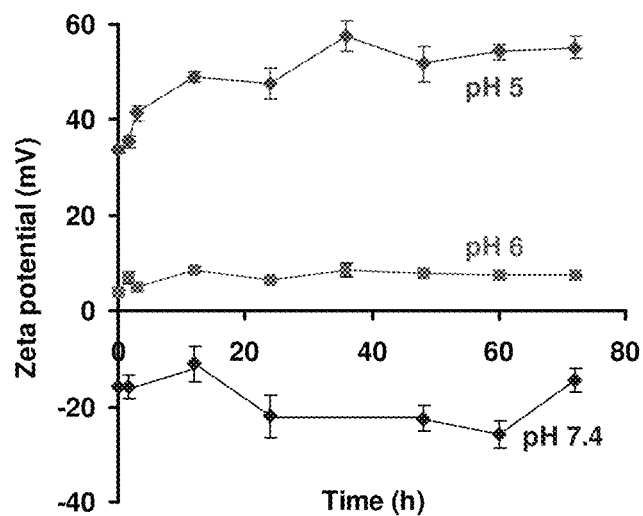
FIG. 6 is a chart of the ξ-potential of TCRNs as a function time at different pHs.
Figure 7:
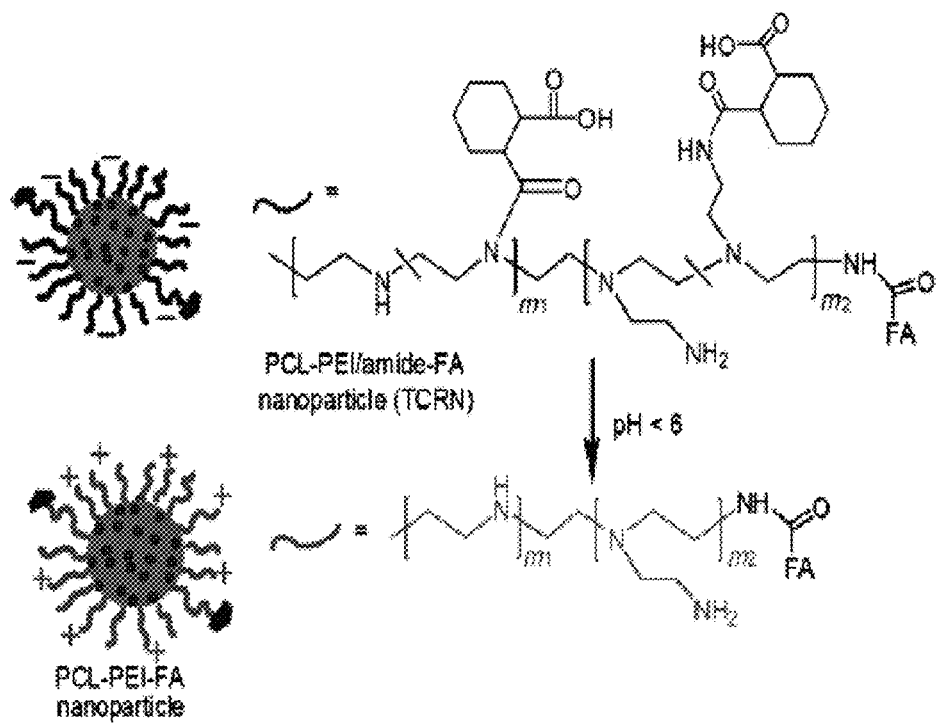
FIG. 7 is a schematic diagram of the targeted charge-reversed nanoparticle (TCRN) and its pH-triggered reversal.

Accordingly, the charge reversal of the PCL-PEI/amide micelles was determined by measuring their z potentials at different acidities (FIG. 6). The micelles of PCL-PEI/amide revealed a z potential of about −20 mV at pH 7.4 even after more than 60 h, indicating that they were always negatively charged as a result of the presence of COOH groups. At pH 5, they immediately became highly positively charged and gradually reached a z potential of about +50 mV in about 10 h. At pH 6, the z potential was about +8 mV. For comparison, the micelles of PCL-PEI were always positively charged. Their z potential was +36.1 mV at pH 5, +18.4 mV at pH 6, and +17.5 mV at pH 7.4. Thus, the PCL-PEI/amide micelles were indeed charge-reversal nanoparticles: they were negatively charged at physiological pH and thus are suitable for in vivo applications. Once localized in solid tumors or lysosomes, the PEI/amides hydrolyze and recover the PEI and the micelles become positively charged. With the folic acid targeting groups, the micelles are named targeted charge-reversal nanoparticles (TCRNs) (Scheme 6—FIG. 7).

Figure 8:
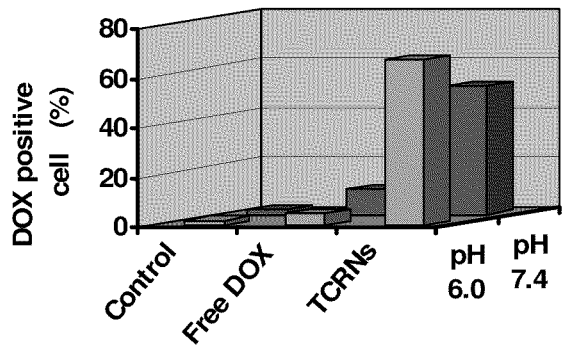
FIG. 8 is a graph of the SKOV-3 cellular uptake of TCRNs/DOX at different pH values. DOX dose: 1 mg/mL; 1 h incubation at 37° C.; results are presented as the mean of three experiments; statistical significance *P<0.05 with respect to all others.

The cellular internalization of TCRNs loaded with DOX (TCRNs/DOX) was measured using flow cytometry (FIG. 8). The percentage of DOX-positive cells cultured with TCRNs/DOX was significantly higher than that cultured with free DOX under the same conditions at pH 7.4. This is a significant improvement compared with reported results in which the cellular uptake of DOX in drug carriers was generally slower than that of free DOX; free DOX enters cell by a rapid diffusion process, while drug carriers enter cells by the slower endocytosis process. FIG. 8 also shows that TCRNs/DOX entered cells faster at pH 6 than at pH 7.4. This observation agrees with the result in FIG. 6, which shows that some positive charges were regenerated on the TCRNs at pH 6. Positive charges promote the cellular internalization through electrostatically adsorptive endocytosis.

Figure 9:
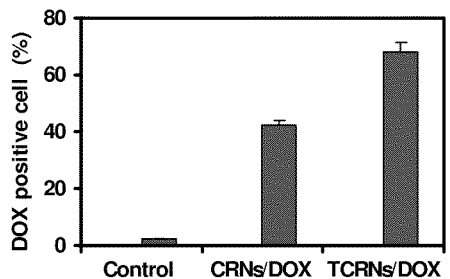
FIG. 9 is a graph of SKOV-3 cellular uptake of DOX-loaded TCRNs and charge-reversal nanoparticles (CRNs) made from PCL-PEI/amide as shown in FIG. 7 but without the folic acid moieties; DOX dose: 0.5 mg/mL; pH 7.4; 2 h incubation at 37° C.; results are presented as the mean of three experiments with standard deviations; *P<0.05 with respect to CRNs/DOX.

The effectiveness of the targeting group folic acid on the TCRNs in binding folate receptors and promoting the cellular uptake was evaluated using SKOV-3 ovarian cancer cells, which are known to overexpress folate receptors. TCRNs were internalized much faster into the cancer cells than the charge-reversal nanoparticles without the folic acid moieties (CRNs) (FIG. 9). This indicates that TCRNs indeed effectively target the folate-receptor-overexpressing cancer cells.

Figure 10:
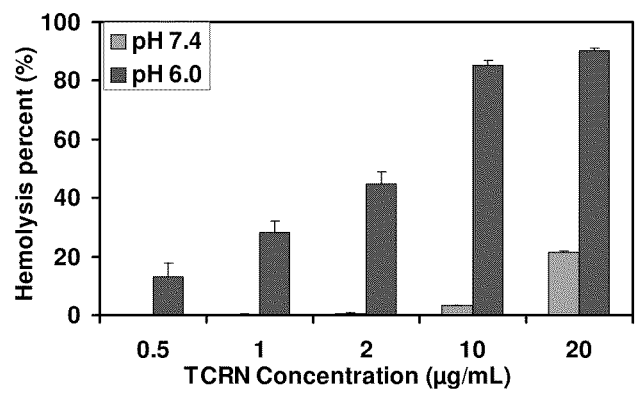
FIG. 10 is a graph of the hemolytic activity of TCRNs on RBCs at pH 6 and 7.4 as a function of TCRN concentration (1 h incubation at 37° C.).

After internalized, the TCRNs must localize in lysosomes to regenerate the PEI layer. The intracellular trafficking of the nanoparticles was analyzed using confocal scanning laser fluorescent microscopy. Most internalized TCRNs were localized in lysosomes. Some TCRNs were not associated with lysosomes, suggesting that these TCRNs might have already escaped from lysosomes within 2 h incubation. The ability of the TCRNs to escape from lysosomes was evaluated by a hemolysis assay. Hemolysis of red blood cells (RBCs) has been used as a measure of the ability of a drug carrier to rupture lysosomes. The hemolysis of TCRNs was evaluated at pH 6 rather than at the lysosomal pH value (pH 4-5) because at this low pH value a significant fraction of RBCs lysed. FIG. 10 shows that at pH 6, TCRNs lysed RBCs even at very low concentrations. This is in agreement with the results shown in FIG. 6. The hydrolysis of PEI/amide at pH 6 produced amine groups carrying positive charges, which caused TCRNs to adsorb on the RBCs and rupture them. One thus can expect that TCRNs would more efficiently rupture lysosomes, where the pH value is 4-5 and TCRNs quickly become fully positively charged. This explains why some of TCRNs were not associated with lysosomes.

FIG. 10 also shows that at neutral pH essentially no RBC hemolysis occurred at TCRN concentrations less than 10 mg/mL, indicating that TCRNs had little interaction with RBCs. Thus, the nanoparticles are suitable for in vivo applications.

The nuclear localization of TCRNs was monitored by observing the SKOV-3 cells cultured with TCRNs loaded with DOX or PKH26 dye using confocal microscopy. After 8 h incubation with SKOV-3 cells, TCRNs/DOX were found very close to or even associated with the nuclear membrane. To further probe the nuclear localization of TCRNs at longer times, the nanoparticles were loaded with PKH26 (TCRNs/PKH26) instead of DOX because DOX released from the TCRNs could enter the nucleus and might produce misleading results. In addition, the cells that had DOX in their nuclei died very quickly. PKH26 is a cell-membrane dye, that is, it preferentially binds the cell membrane. Thus, it can only be delivered to the nucleus by the TCRNs. It shows no apparent toxic effect to cells. At 12 h, TCRNs/PKH26 localized in some nuclei but mostly associated with nuclear membranes. After 24 h incubation with the SKOV-3 cells, many TCRNs/PKH26 appeared in the nuclei. z-Serial images of the cell further confirmed the nuclear localization of the TCRNs/PKH26. This result proves that in contrast to nanoparticles with a PEG corona, which are retained in the lysosomes and other subcellular compartments, TCRNs could indeed enter the nuclei of the cancer cells.

Figure 11:
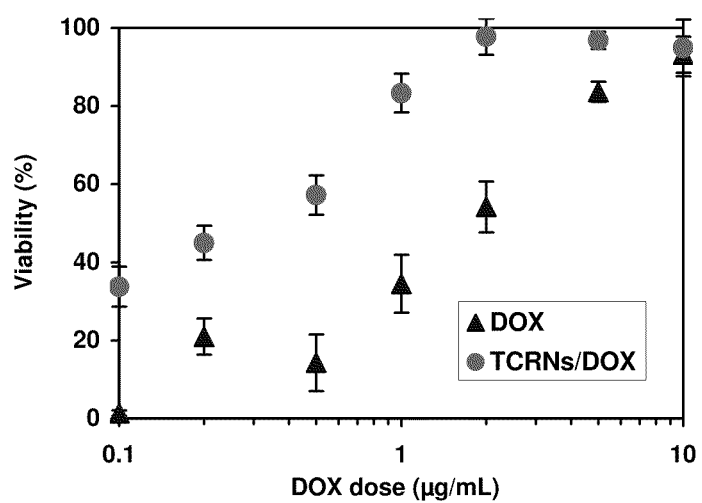
FIG. 11 is a graph of the cytotoxicity of DOX, TCRNs/DOX, and blank TCRNs to SKOV-3 ovarian cancer cells as a function of the DOX or TCRN dose; the results are presented as the mean of four experiments with standard deviations.
Figure 12:
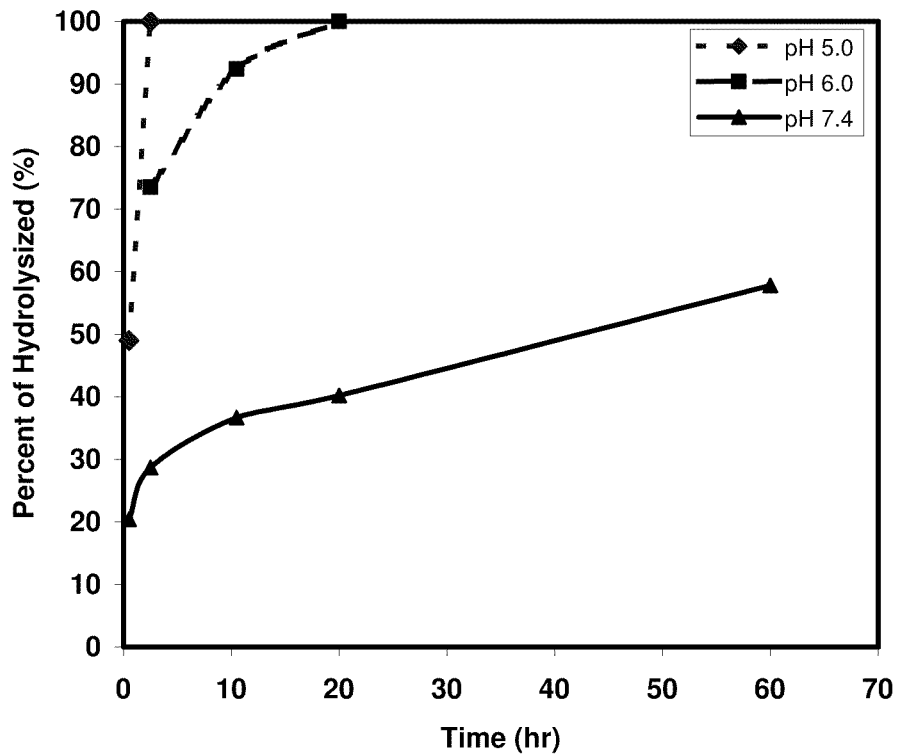
FIG. 12 is a chart of the pH-dependent hydrolysis of the amide bond shown in Scheme 1.
Figure 13:
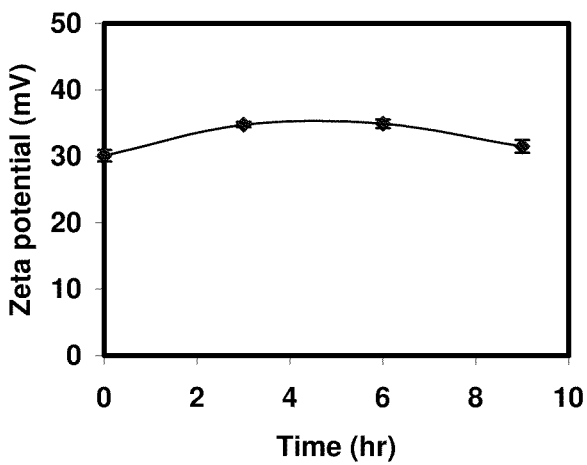
FIG. 13 is a chart of the zeta-potential as a function of time at pH 5 of micelles made from PCL-PEI-An.
Figure 14:
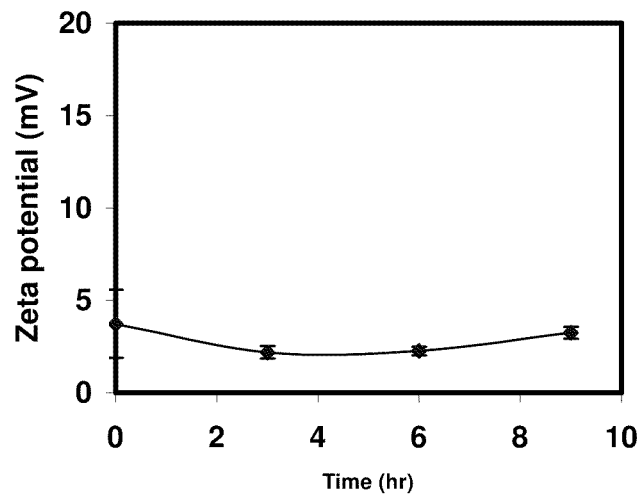
FIG. 14 is a chart of the zeta-potential as a function of time at pH 6 of micelles made from PCL-PEI-An.
Figure 15:
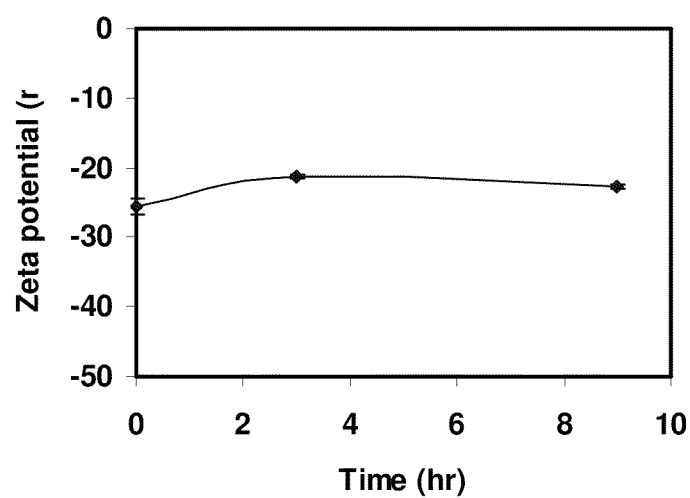
FIG. 15 is a chart of the zeta-potential as a function of time at pH 7.4 of micelles made from PCL-PEI-An.

The in vitro cytotoxicity of DOX encapsulated in TCRNs (TCRNs/DOX) was evaluated by measuring the IC50 using the MTT assay (FIG. 11; MTT: 3-(4,5-dimethylthiazol-2-yl)-2,5-diphenyltetrazolium bromide). TCRNs alone showed no detectable cytotoxicity even at high doses. The IC50 of free DOX was about 1.5 mg/mL, and it decreased to 0.23 mg/mL when it was encapsulated in TCRNs (FIG. 11). This is different from most other reported nanoparticles as DOX carriers, in which DOX in the nanoparticles showed a lower cytotoxicity than free DOX This comparison shows that the TCRNs could efficiently cross the cell membrane, escape from the lysosomes, and localize and deliver DOX in the nucleus to result in a greater cytotoxicity.

In summary, we have demonstrated a negative-to-positive charge-reversal technique for preserving primary and secondary amines for in vivo nuclear drug delivery. TCRNs composed of folic acid functionalized PCL-PEI/amide are negatively charged in neutral solution but quickly become positively charged at pH 6 and highly positively charged at pH 5. The hydrolysis kinetics indicate that amides with β-carboxylic acids can hydrolyze in acidic conditions to regenerate the amines, giving rise to a negative-to-positive charge reversal. These recovered amines carry positive charges, which can effectively enhance the cellular uptake of the nanoparticles, and thereafter direct the TCRNs to localize in the nucleus. In vitro experiment shows that TCRNs/DOX are more effective in killing SKOV-3 cancer cells than free doxorubicin is.

Example 10

Figure 16:
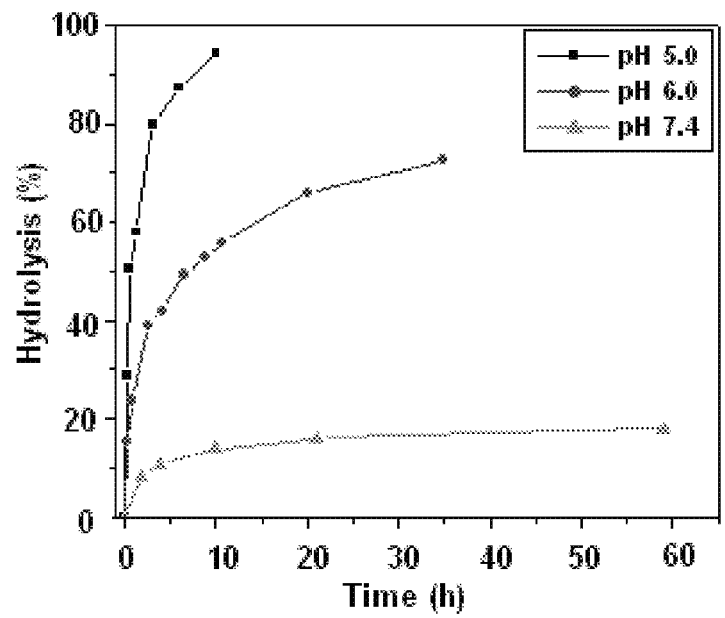
FIG. 16 is a graph of the overall hydrolytic kinetics of the amides in the PLL/amide at different acidities at 37° C.
Figure 17:
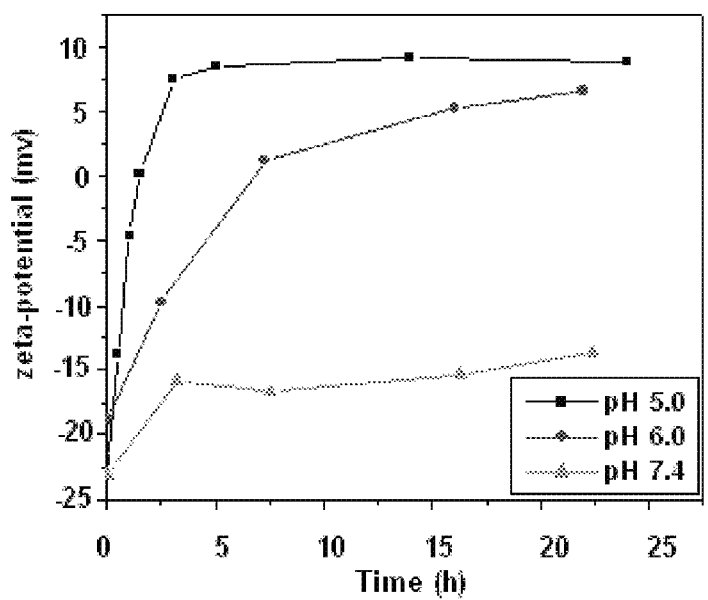
FIG. 17 is a graph of the ξ-potential of PLL/amide as a function time at different pHs.

An example of charge-reversal poly(L-lysine) (PLL) amide is shown in Scheme 7. It can be made by the reaction of PLL with the corresponding anhydride. The PLL/amide was dissolved in buffers at pH 7.4, 6 or 5 and the hydrolysis of the amide was monitored by NMR. At pH 7.4, about 20% the amide hydrolyzed even after 80 h, but at pH 5, all the amide bonds hydrolyzed within 10 h. The hydrolysis at pH 6 was slower than that at pH 5 but much faster that at pH 7.4 (FIG. 16). The corresponding charge reversal of the PLL/amide was determined by measuring its ξ-potentials using Nano-ZS (Malvern). PLL itself had a ξ-potential of 15±2 mV independent of pH. The PLL/amide gradually became positively charged with a ξ-potential of about +10 mv at pH 5 and +5 mv at pH 6 (FIG. 17). The PLL/amide remained negatively charged at pH 7.4 even after 72 h, which makes it suitable for in vivo applications.

Scheme 7: Charge-reversal polylysine

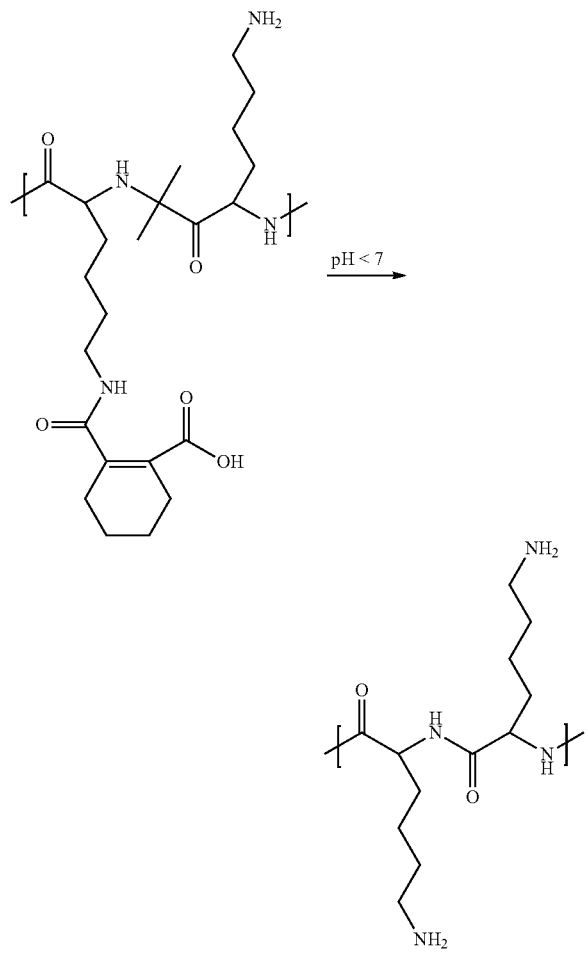

Example 11

Liposomes, nanoparticles or micelles or microparticles with outer layers containing hydrolysable amides are neutral or negatively charged at neutral pH but become positively charged at acidic pHs. A model polymer, polycaprolactone (Mn=3800)-block-PEI (Mn=1800) (PCL-PEI) was synthesized. Its PEI block reacted with 1,2-cyclohexanedicarboxylic anhydride to convert all or part of the primary and secondary amines into their amides (PCL-PEI/amide) (FIG. 3). It forms micelles of about one hundred nanometers.

Figure 1:
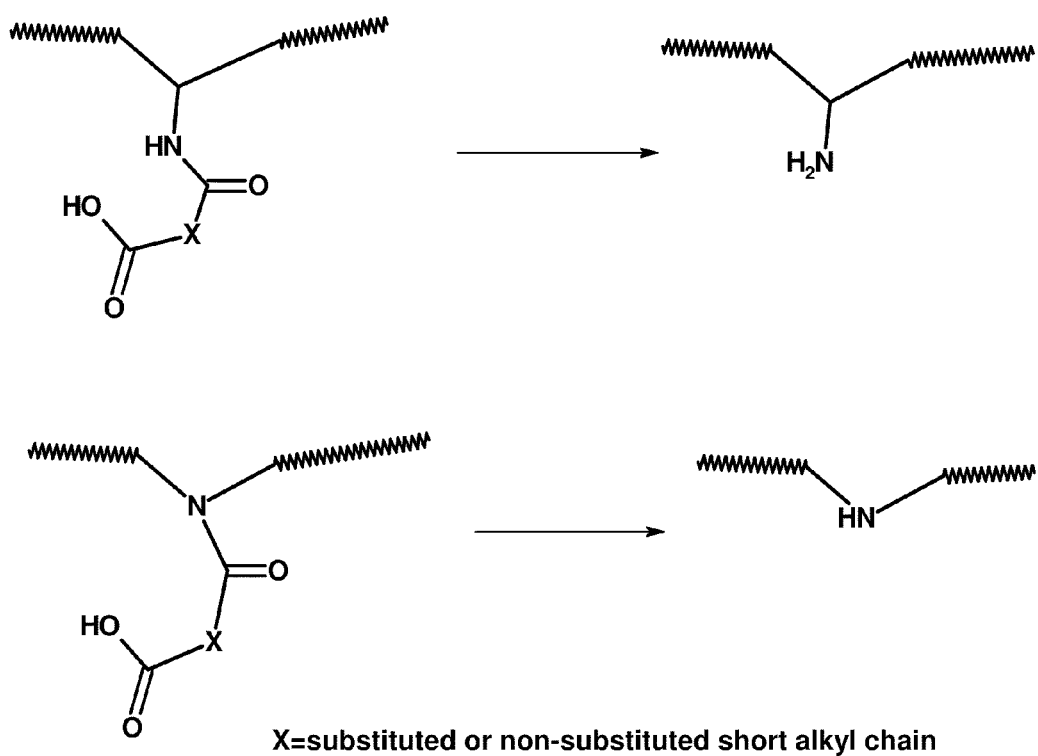
FIG. 1 is a schematic diagram of charge reversal by amide hydrolysis.
Figure 2:
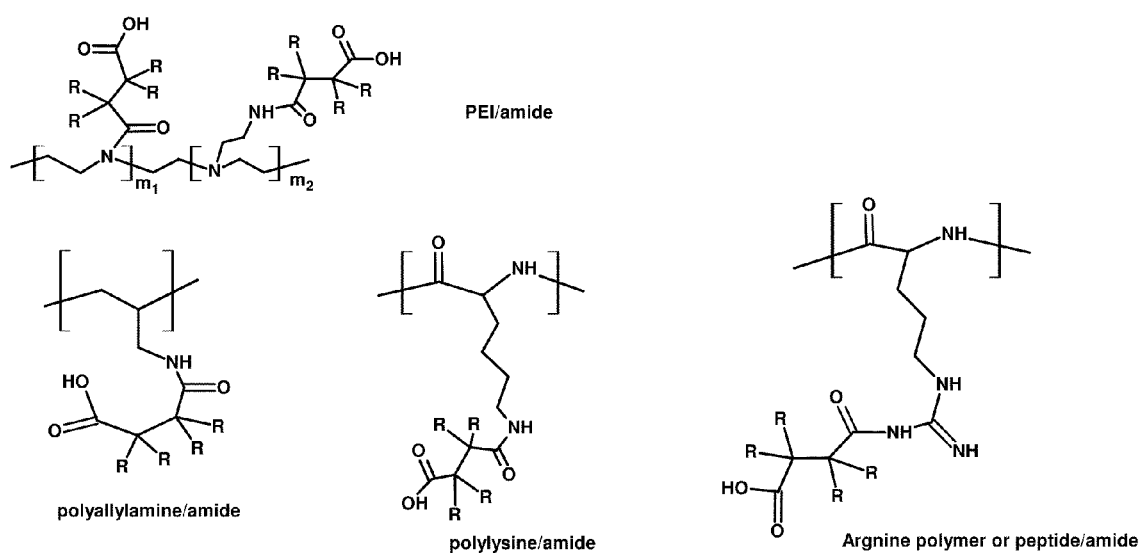
FIG. 2 is a schematic diagram of examples of charge reversible polymers or peptides.

The degree of the amidization was optimized and it was found that the PEI block with 20% of the primary and secondary amines converted to the amides was optimal in terms of the charge reversal kinetics of the resulting nanoparticles (FIG. 2). If all the primary and secondary amines were reacted to their amides, the resulting nanoparticles could not rapidly become highly negative charged at low pH. The folic acid moieties were also conjugated to the PEI block to form PCL-b-PEI/amide-FA (FIG. 2) for folate receptor targeting. It was estimated from the NMR spectra that there was 0.79 folic acid molecule per PCL-PEI chain on average. The PCL-PEI/amide-FA formed nanoparticles of about 210 nm in diameter in water. The nanoparticles were about 120 nm in diameter if loaded with 14.6 wt % DOX. Transmission electron microscopy (TEM) images showed that these nanoparticles were spherical.

Figure 18:
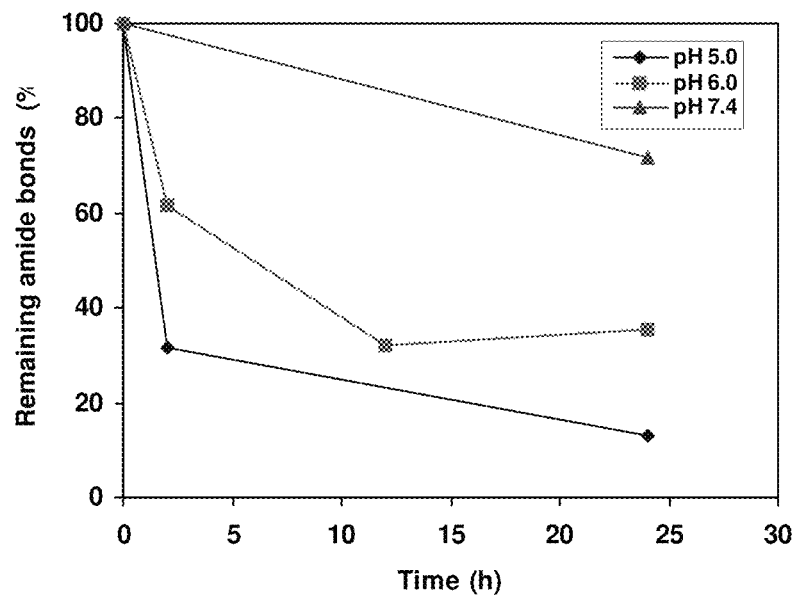
FIG. 18 is a graph of the overall hydrolytic kinetics of the amides in the PCL-PEI/amide-FA at different acidities at 37° C.

The hydrolysis kinetics of the amides in the PCL-PEI/amide was determined by dispersing the nanoparticles in solution at pH 7.4, 6.0 or 5.0. The concentration of free 1,2-cis-cyclohexanedicarboxylic acid in the solution hydrolyzed from the PEI/amide was determined by NMR using DMF as the internal reference, and the percent of the unhydrolyzed amides was calculated accordingly. FIG. 18 shows the overall hydrolysis kinetics of the amides of the primary and secondary amines in the PEI block. The amides hydrolyzed about 70% at pH 5.0 and 40% at pH 6.0 in 2 h. At pH 7.4, only about 25% amide bond hydrolyzed even after 24 h. The amides hydrolyzed more than 50% and 75% at pH of 6.0 and 5.0 respectively, after 24 h.

Figure 19:
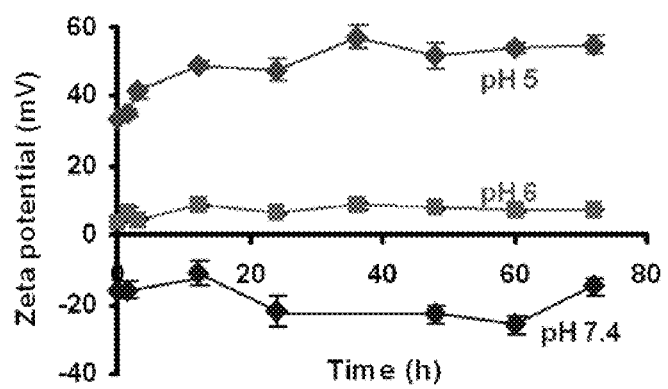
FIG. 19 is a graph of the ξ-potential of the PCL-PEI/amide nanoparticles at 37° C. as a function of time at different acidities.

Accordingly, the charge reversal of the PCL-PEI/amide micelles was determined by measuring their ξ-potentials at different acidities (FIG. 19). The micelles of PCL-PEI/amide had a ξ-potential of about −20 mV at pH 7.4 even after more than 60 h, indicating that they were always negatively charged due to the presence of —COOH groups. At pH 5, they immediately became highly positively charged, and gradually reached a ξ-potential of about +50 mV in about 10 h. At pH 6, the ξ-potential was about +8 mV. For comparison, the micelles of PCL-PEI were always positively charged. Their ξ-potential was +36.1 mV at pH 5, +18.4 mV at pH 6 and +17.5 mV at pH 7.4. Thus, the PCL-PEI/amide micelles were indeed charge reversal: they were negatively charged at the physiological pH and thus suitable for in vivo applications. Once localized in solid tumors or lysosomes, the PEI/amides are expected to hydrolyze and recover the PEI, and the micelles become positively charged. With the folic acid targeting groups, the micelles are named targeted charged reversal nanoparticles (TCRNs) (FIG. 2).

Example 12

The nuclear localization of charge-reversal nanoparticles was demonstrated using the PCL-PEI/amide nanoparticles by observing the SKOV-3 cells cultured with particles loaded with DOX or PKH26 fluorescent dye using confocal microscopy. After 12 h incubation with SKOV-3 cells, the nanoparticles loaded with PKH26 localized in some nuclei but mostly associated with nuclear membranes. After 24 h incubation with the SKOV-3 cells, many nanoparticles/PKH26 appeared in the nuclei. This proved that, in contrast to the conventional nanoparticles with PEG corona, which are retained in the lysosomes and other subcellular compartments, the charge reversal nanoparticles could indeed enter the nuclei of the cancer cells, which can potentially enhance the efficiency of the drug.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A method of delivering a drug to a solid tumor of a subject, or to lysosomes of a subject, comprising the following steps:
   (a) providing a first compound having primary and secondary amines that are protected as easily hydrolysable amide bonds;
   (b) acidifying said compound under conditions effective to hydrolyze the amide bonds of the first compound, thereby forming a second compound, whereby said second compound spontaneously forms micelles;
   (c) incorporating a drug into the micelles; and
   (d) injecting the drug-containing micelles into a subject having a solid tumor or lysosomes.

2. A method of drug delivery as defined in claim 1, wherein the drug is releasably bound to the second compound.

3. A method of drug delivery as defined in claim 1, wherein the first compound is selected from the group consisting of peptides, proteins and other biopolymers that are negatively charged or neutral at pH higher than 7, but become positively charged at pH lower than 7.

4. A method of drug delivery as defined in claim 3, further comprising the step of incorporating a bioactive agent into the micelles and wherein the peptide, protein and other biopolymer hydrolyses at a delivery site of the bioactive agent to release the drug and bioactive agent at the delivery site.

5. A method of drug delivery as defined in claim 1, wherein the first compound comprises particles that are negatively charged or neutral at pH higher than 7, but become positively charged at pH lower than 7.

6. A method of drug delivery as defined in claim 5, further comprising incorporating a bioactive agent inside the particles and wherein at least a portion of the particles hydrolyse at a delivery site of the bioactive agent to release the bioactive agent and drug at the delivery site.

* * * * *